United States Patent [19]

Snoke et al.

[11] Patent Number: 5,399,164
[45] Date of Patent: Mar. 21, 1995

[54] CATHETER HAVING A MULTIPLE DUROMETER

[75] Inventors: Phillip J. Snoke, Atlanta; David S. Rowley; David G. Lincoln, both of Smyrna; Kirk W. Charles, Austell, all of Ga.

[73] Assignee: Catheter Imaging Systems, Atlanta, Ga.

[21] Appl. No.: 970,490

[22] Filed: Nov. 2, 1992

[51] Int. Cl.⁶ ............................................. A61M 37/00
[52] U.S. Cl. ...................................... 604/95; 604/282; 604/264
[58] Field of Search ................ 604/264, 95, 280, 281, 604/282; 128/656, 657, 658, 772

[56] References Cited

U.S. PATENT DOCUMENTS

| | | |
|---|---|---|
| 922,985 | 5/1909 | Wappler . |
| 3,470,876 | 10/1969 | Barchilon ............................ 604/95 |
| 3,892,228 | 7/1975 | Mitsui ................................. 128/4 |
| 3,948,251 | 4/1976 | Hosono ............................... 128/4 |
| 4,273,111 | 6/1981 | Tsukaya ......................... 604/95 X |
| 4,279,245 | 7/1981 | Takagi et al. ....................... 128/4 |
| 4,327,723 | 5/1982 | Frankhouser . |
| 4,390,012 | 6/1983 | Mizumoto ........................... 128/4 |
| 4,417,886 | 11/1983 | Frankhouser et al. . |
| 4,483,326 | 11/1984 | Yamaka et al. ..................... 128/4 |
| 4,515,592 | 5/1985 | Frankhouser . |
| 4,543,090 | 9/1985 | McCoy ............................... 604/95 |
| 4,577,621 | 3/1986 | Patel .................................. 128/4 |
| 4,580,551 | 4/1986 | Siegmund et al. ................. 128/4 |
| 4,587,972 | 5/1986 | Morantte, Jr. ................... 128/303 |
| 4,625,713 | 12/1986 | Hiraoka ............................. 128/4 |
| 4,644,960 | 2/1987 | Johans . |
| 4,745,908 | 5/1988 | Wardle .............................. 128/6 |
| 4,748,969 | 6/1988 | Wardle .............................. 128/4 |
| 4,753,222 | 6/1988 | Morishita .......................... 128/4 |
| 4,758,222 | 7/1988 | McCoy ............................... 604/95 |
| 4,793,326 | 12/1988 | Shishido ............................ 128/4 |
| 4,815,450 | 3/1989 | Patel .................................. 128/6 |
| 4,834,710 | 5/1989 | Fleck . |
| 4,844,053 | 7/1989 | Dittrich ............................. 128/4 |
| 4,890,602 | 1/1990 | Hake ................................. 128/4 |
| 4,893,613 | 1/1990 | Hake ................................. 128/4 |
| 4,906,230 | 3/1990 | Maloney et al. ................... 604/95 |
| 4,911,148 | 3/1990 | Sosnowski et al. ................ 128/6 |
| 5,004,456 | 4/1991 | Botterbusch et al. . |
| 5,058,568 | 10/1991 | Irion et al. ......................... 128/4 |
| 5,125,906 | 6/1992 | Fleck . |
| 5,199,950 | 4/1993 | Schmitt et al. .................... 604/95 |

*Primary Examiner*—John D. Yasko
*Attorney, Agent, or Firm*—Bell, Seltzer, Park & Gibson

[57] ABSTRACT

The catheter has a housing of such a size as to be readily held in the hand of the user, and a tubular proximal portion connected to and extending from the housing. The proximal portion is formed of a flexible polymeric material. The distal portion is coaxial with and is adjacent to the proximal portion. The distal portion is also formed of a flexible polymeric material and it has substantially the same outer circumference as the proximal portion. The distal portion is more flexible than the medial portion. A pair of control wires extend longitudinally through the proximal and distal portions and parallel to the axis of the coaxial portions for bending the flexible portions in response to movement of the control wires. A control is carried by the housing for controlling the movement of the control wires to thereby bend the flexible portions and remotely manipulate the catheter within a human body.

30 Claims, 2 Drawing Sheets

U.S. Patent     Mar. 21, 1995     Sheet 1 of 2     5,399,164
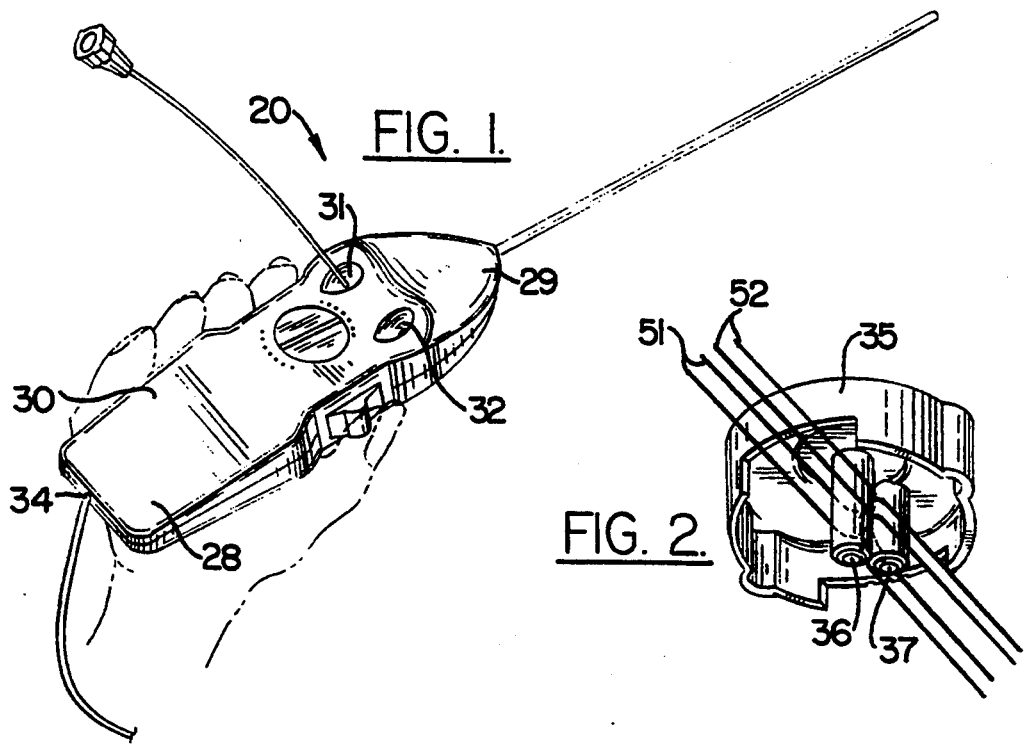
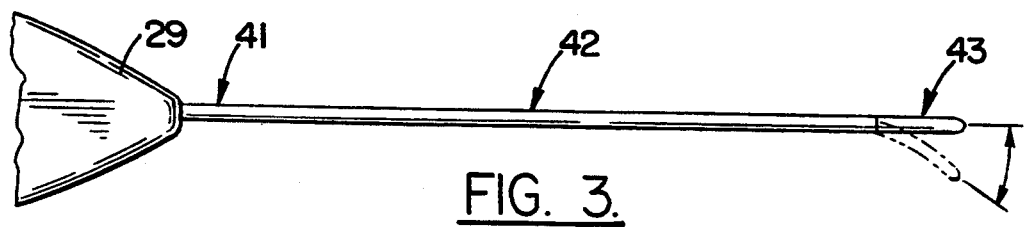
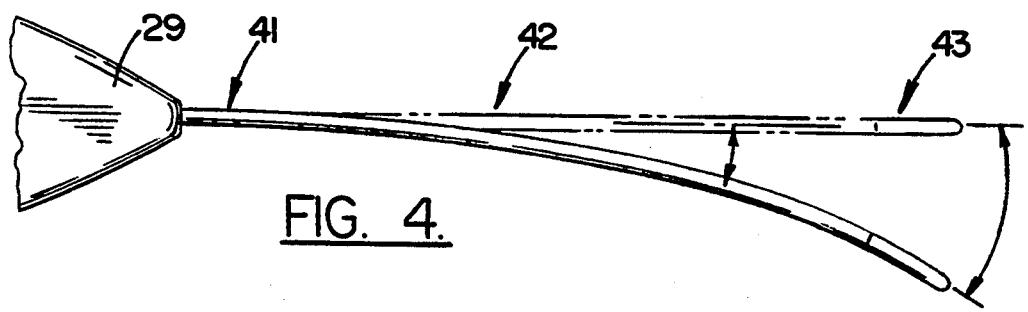

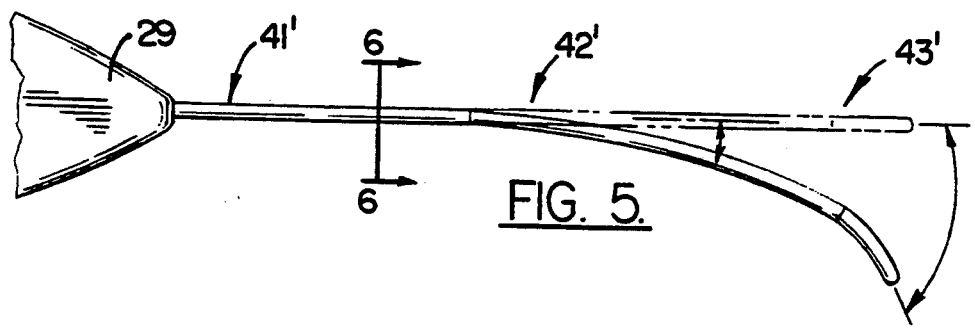
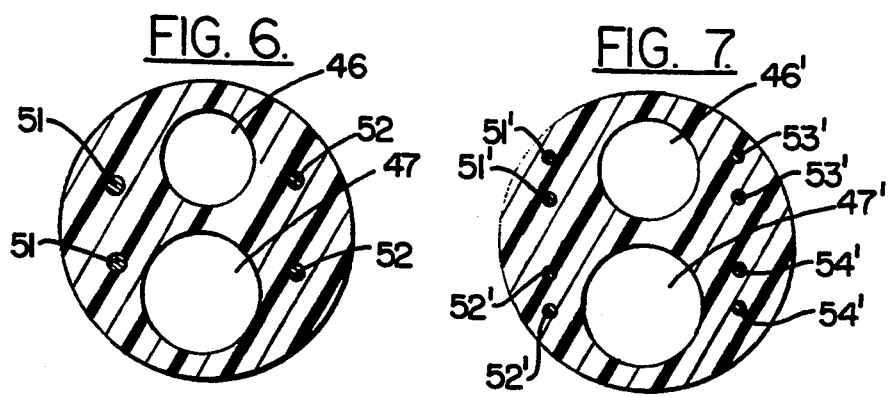
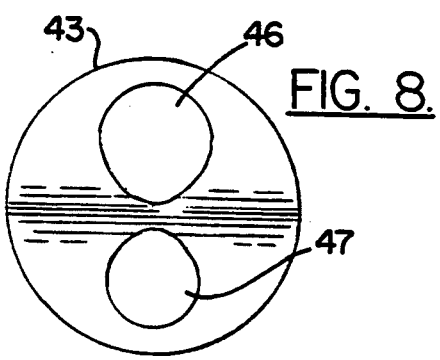
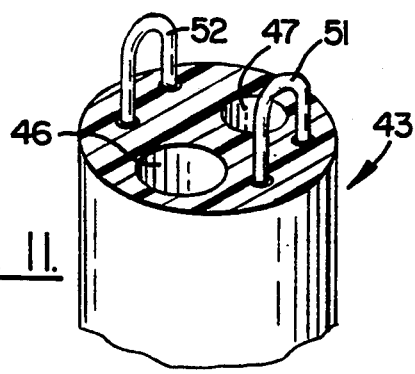
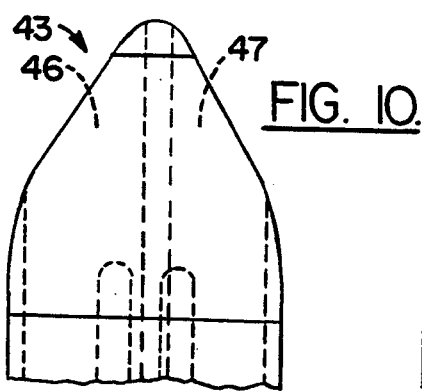
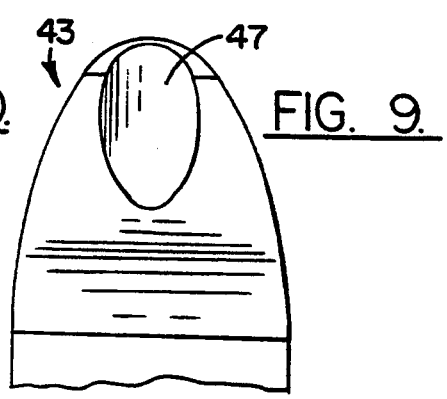

CATHETER HAVING A MULTIPLE DUROMETER

RELATED APPLICATIONS

This application is related to copending U.S. patent application Ser. No. 07/908,403 filed on Jul. 6, 1992.

FIELD OF THE INVENTION

This invention relates to medical catheters, and more particularly to a catheter having an elongated tube of variable hardness.

BACKGROUND OF THE INVENTION

Various commercially available endoscopes and catheters exist for introducing into body vessels or cavities a variety of surgical tools, fluids, and other materials, such as radiographic contrast materials, angioplasty balloons, fiberoptic scopes, laser lights, and cutting instruments. Also, various techniques and systems have been developed for guiding or steering the catheters in the body vessels or cavities for use of these tools, fluids, and other materials. Therapeutic treatments may be made by inserting surgical instruments or fluid through a treatment channel of the endoscope or catheter.

Several devices have been developed for controlling movement in a portion of the catheter by use of wiring systems or linked segments within the catheter. Examples of these devices may be seen in U.S. Pat. No. 3,948,251 by Hosono entitled "*Flexible Tube Endoscope*"; U.S. Pat. No. 4,279,245 by Takagi et al. entitled "*Flexible Tube*"; U.S. Pat. No. 5,058,568 by Irion, et al. entitled "*Flexible Endoscope*"; U.S. Pat. No. 4,844,053 by Dittrich entitled "*Flexible Tubular Device*"; U.S. Pat. No. 4,753,222 by Morishita entitled "*Endoscopic Flexible Tube*"; U.S. Pat. No. 4,580,551 by Siegmund, et al. entitled "*Flexible Plastic Tube for Endoscopes And The Like*"; and, U.S. Pat. No. 4,911,148 by Sosnowski, et al. entitled "*Deflectable-End Endoscope With Detachable Flexible Shaft Assembly*".

Other devices have been developed which control the movement of the catheter by insertion of an instrument into a channel or lumen of the catheter. Examples of such devices may be seen in U.S. Pat. No. 922,985 by Wappler entitled "*Endoscope*"; U.S. Pat. No. 4,390,012 by Mizumoto entitled "*Rigid Type Endoscope*"; U.S. Pat. No. 4,577,621 by Patel entitled "*Endoscope Having Novel Proximate and Distal Portions*"; U.S. Pat. No. 4,587,972 entitled "*Device For Diagnostic And Therapeutic Intravascular Intervention*"; U.S. Pat. No. 4,625,713 by Hiraoka entitled "*Instrument Incorporated In A Resectoscope*"; U.S. Pat. No. 4,745,908 by Wardie entitled "*Inspection Instrument With Flexible Shaft Having Deflection Compensation Means*"; U.S. Pat. No. 4,748,969 by Wardle entitled "*Multi-Lumen Core Deflecting Endoscope*"; and U.S. Pat. No. 4,793,326 by Shishido entitled "*Endoscope Having Insertion End Guide Means*". These devices, although illustrating various control techniques, do not provide ease of insertion and control to the hand of the physician or user.

Other catheters using various other control techniques may be seen in U.S. Pat. No. 3,892,228 by Mitsui entitled "*Apparatus For Adjusting The Flexing Of The Bending Section Of An Endoscope*"; U.S. Pat. No. 4,483,326 by Yamaka, et al. entitled "*Curvature Control Mechanism In Endoscopes*"; U.S. Pat. No. 4,543,090 by McCoy entitled "*Steerable and Aimable Catheter*"; U.S. Pat. No. 4,815,450 by Patel entitled "*Endoscope Having Variable Flexibility*"; U.S. Pat. No. 4,890,602 by Hake entitled "*Endoscope Construction with Means For Controlling Rigidity and Curvature of Flexible Endoscope Tube*"; U.S. Pat. No. 4,906,230 by Maloney, et al. entitled "*Steerable Catheter Tip*"; and, U.S. Pat. No. 4,893,613 by Hake entitled "*Endoscope Construction With Means For Controlling Rigidity And Curvature Of Flexible Endoscope Tube*". These prior control systems attempted to control portions of the catheter by inserting instruments therein or inserting wires or other control mechanisms within a tube of the catheter. Like the other devices, however, the mechanisms for controlling the catheters are often awkward and bulky for insertion and control purposes.

Thus, there is still a need for a catheter imaging apparatus that allows for ease of insertion into the body vessel or cavity and also provides control and manipulation of the catheter while simultaneously using surgical tools, such as fiberoptic scopes or the like, and fluids needed for medical operations to thereby allow the physician to positionally locate, isolate, and view problem areas within the body vessel or cavity.

SUMMARY OF THE INVENTION

Therefore an object of the present invention is to provide a catheter that can be more easily inserted into a vessel or cavity of the human body and provide control and flexibility for the user. The catheter of the invention advantageously provides an elongate tube having portions of varying durometer hardness to improve the ease of insertion into a body vessel or cavity and also provide improved control of the catheter.

These and other objects, features, and advantages of the present invention are set forth more fully below. In particular, the catheter has a housing of such a size as to be readily held in the hand of the user, and a tubular proximal portion connected to and extending from the housing. The proximal portion is formed of a flexible polymeric material. The distal portion is coaxial with and adjacent to the proximal portion. The distal portion is also formed of a flexible polymeric material and has substantially the same outer circumference as the proximal portion. The distal portion is more flexible than the proximal portion. A pair of control wires, extend longitudinally through the proximal and distal portions and parallel to the axis of the coaxial portions for bending the flexible portions in response to movement of the control wires. A control wheel is carried by the housing for controlling the movement of the control wires to thereby bend the flexible portions and remotely manipulate the catheter within a human body.

BRIEF DESCRIPTION OF THE DRAWINGS

Some of the objects and advantages of the present invention having been stated, others will become apparent as the description proceeds when taken in conjunction with the accompanying drawings, in which:

FIG. 1 is a perspective view of the catheter having a multiple durometer hardness according to the present invention;

FIG. 2 is an enlarged view of the control wheel and control wires of the catheter according to the present invention;

FIG. 3 is a top plan view of the catheter with parts broken away for clarity showing the flexible distal portion being more flexible than a proximal portion of the elongate tube;

FIG. 4 is a top plan view of a catheter illustrating the movement of the proximal, medial and distal portions of the elongate tube in response to the control wheel;

FIG. 5 is a top plan view of another embodiment of the catheter having proximal, medial, and distal portions of an elongate tube and illustrating the flexibility of the movement of these portions;

FIG. 6 is an enlarged cross-sectional view taken along line 6—6 of FIG. 5 illustrating the working lumens and the control wires, as well as illustrating the similar outer circumference of the elongate tube of the catheter;

FIG. 7 is an enlarged cross-sectional view of another embodiment of the elongate tube of the catheter having additional control wires on each side of the working lumens for further control of the catheter;

FIG. 8 is an enlarged top end view of the catheter from the distal portion;

FIG. 9 is an enlarged side plan view of the distal portion of the catheter;

FIG. 10 is an enlarged side plan view of a distal portion of a catheter having dashed lines for indicating the working lumens and the wires within the distal portion; and FIG. 11 is an enlarged cut away view of distal portion illustrating the insertion of the control wires within the catheter.

DESCRIPTION OF A PREFERRED EMBODIMENT

The present invention now will be described more fully hereinafter with reference to the accompanying drawings in which a preferred embodiment of the invention is shown. Like numbers refer to like elements throughout.

Referring now to the drawings, FIG. 1 is a perspective view of the catheter broadly designated at 20 having multiple durometer hardness. The catheter 20 has a housing 30 of such a size as to be readily held in the hand of a user. The catheter 20 has an elongate tube 40 connected to the housing 30 and extending from an end 29 thereof. The one piece elongate tube 40 is integrally formed of a material having sufficient stiffness to maintain the elongate tube 40 along a substantially straight axis in the absence of an external force applied thereto. The housing 30 has access ports 31, 32 for permitting access to a pair of working lumens 45, 46 (shown in FIG. 6) within the opposite end 28 of the elongate tube 40. An access port 34 within the housing 30 also provides access to one of the lumens 45 or 46 for a fiberscope or the like.

FIGS. 2–5, illustrate the controlled movement of the flexible portions of the catheter 20 having variable hardness. FIG. 2 is an enlarged view of the control means shown in the form of control wheel 35 carried by the housing 30 and having stem portions 36, 37 connected thereto. Means for adjusting the flexibility of the elongated tube 40, shown in the form of control wires 51, 52, engage the stem portions 36, 37 of the control wheel 35 to bend thereby manipulate various flexible portions of the elongate tube 40 of a catheter 20. The control wires 51, 52 cross and wrap around the stem portions 36, 37 as illustrated in FIG. 2 and attach to a portion of the housing 30. It will be apparent that various other attaching or engaging locations may also be used, such as attaching the wires 51, 52 to the control wheel 35 in some manner.

FIG. 3 illustrates a top plan view of the catheter 20 with parts broken away for clarity and showing the proximal portion 41, the medial portion 42, and a distal portion 43. The phantom view and the directional arrow illustrate the controlled movement of the distal portion 43 of the catheter 20. The movement of the distal portion 43 of the catheter 20 without the medial 42 or the proximal 41 portions moving illustrates the multiple durometer or hardness aspects of the polymeric material of the catheter. The elongate tube 40 is typically formed of one type of polymeric material, preferably a thermoplastic such as polyurethane, but other polymeric materials apparent to those skilled in the art may also be used.

FIG. 4 further illustrates how the medial 42 and proximal 41 portions bend more and are more flexible than the catheter movement illustrated in FIG. 3. This flexibility depends on the hardness characteristics of the polymeric material used to form the various portions 41, 42, 43 of the elongate tube 40. For forming the elongate tube 40 of the catheter 20, the polymeric material is extruded having characteristics such to form the elongate tube 40 having cross-sectional profiles as illustrated in FIGS. 6 or 7. The extruding process provides the formation of the proximal 41, medial 42, and/or distal 43 portions having varying hardness by use of polymeric material such as polyurethane having different durometer characteristics. Typically, the proximal 41, medial 42, and distal 43 portions have substantially the same outer circumference throughout the elongate tube 40. The extrusions are cut to the desired length and are integrally joined as one-piece using sonic welding or radio frequency ("RF") welding. Other various joining techniques, such as solvent bonding, apparent to those skilled in the art may also be used. The lumens 46, 47 are kept in line by using a mandrel of the proper size to ensure proper alignment. In addition, molding or other tube forming techniques, as well as the extruding discussed herein, may be used to form the various tube portions 41, 42, 43. If the tube portions are molded, various hardening techniques apparent to those skilled in the art may also be used to form the varying flexibility of the tube portions.

FIG. 5 illustrates another embodiment of the catheter 20' taken from the top plan view with parts broken away for clarity illustrating controlled movement of the tubular coaxial proximal 41', medial 42', and distal 41' portions. In this embodiment, the control wires 51 and 52 are able to move the distal portion at a greater angular attitude than the medial portion 42' as illustrated by the directional arrows. The embodiment of FIGS. 3–5 use the control wires 51, 52 to change the angular attitude of the distal 43 and medial 42 portions from the substantial straight axis to thereby remotely manipulate these portions by use of the control wheel 35. It will be apparent to those skilled in the art that various other means may be used to control the movement of the various portions 41, 42, 43 of the elongate tube 40 or remotely manipulate the wires or the like. Further, the control wires may only extend into various portions 41, 42, or 43 of the elongate tube 40 for changing the angular attitude of the medial 42 or proximal 40 portions from the substantially straight axis separately from any changes in the angular attitude of the distal portion to thereby manipulate the medial 42 or the proximal portion.

FIGS. 6 and 7 illustrate the location of the working lumens 46, 47 extending parallel to the axis of the coaxial proximal 41 medial and distal 43 portions and the control wires 51, 52 within the elongate tube 40. FIG. 6 is an enlarged cross sectional view taken along line 6—6 of FIG. 5. FIG. 6 illustrates that working lumens 46, 47, of the catheter 20. It also illustrates the location of the control wires 51, 52 in the preferred embodiment. As previously discussed the various portions 41, 42, 43, of the elongate tube 20 have substantially the same outer circumference and are joined at ends thereof by one or more of the various techniques described above. FIG. 7 is a cross-sectional view similar to FIG. 6 of another embodiment of the catheter 20' having control wires 51', 52', 53', 54' to provide additional control of the catheter 20. This embodiment can be used to separately change the angular attitude of the various portions 41, 42, 43 of the elongate tube 40. The control wires 53', 54', for example, may only extend longitudinally into the medial portion 42 to thereby separately bend and manipulate that portion of the catheter 20 with respect to the distal portion 43.

FIGS. 8-11 illustrate views of the distal portion 43 of the catheter 20 and the construction thereof. FIG. 8 is a top plan view of the distal portion 43 of the catheter 20 illustrating the working lumens 46, 47, for access of a fiberoptic scope or the like into a vessel or cavity of the human body. FIG. 9 is a side plan views illustrating one of the lumens 47. FIG. 10 is another side plan views having phantom views of the location of the lumens 46, 47 and the control wires 51, 52.

FIG. 11 is an enlarged cross-sectional view illustrating the insertion of control wires 51, 52, prior to forming the tip of the distal portion 43 to thereby form a converging tip as illustrated in FIGS. 8-10 for ease of insertion and access into and through a body vessel, cavity, skin or tissue. The control wires 51, 52 are inserted into the wire channels of the various portions 41, 42, 43 and looped through the distal portion 43. The wires 51, 52 are held under tension as the distal portion 43 is inserted into a tipping die. The die is heated and shaped to form the convergent tip and then cooled to form the tip of the flexible distal portion 43 as illustrated in FIGS. 8-10. The wires 51, 52 preferably need to be fixed to the elongate tube 40 in some manner so that the movement of the control wheel 35 or the like moves the wires 51, 52 to thereby bend and manipulate the flexible portions of the catheter 20. Numerous techniques can be used to fix the wires 51, 52 to the elongate tube 40 such as RF welding or sonic welding ends of the wires 51, 52 to a portion, such as the distal portion 43 of the elongate tube 40. As illustrated in the preferred embodiment of FIG. 11, the looping of the wires 51, 52 through the wire channels in the distal portion 43 secures the wires to a portion of the elongate tube 40 and also reduces the slippage of the wires as the wires 51, 52 are moved longitudinally with respect to one another to bend the various portions 41, 42, 43 of the elongate tube 40.

In the drawings and specification, there have been disclosed typical preferred embodiments of the invention and, although specific terms are employed, they are used in a generic and descriptive sense only and not for the purposes of limitation, the scope of the invention being set forth in the following claims.

That which is claimed is:

1. A catheter for easily inserting into a vessel or cavity of the human body to thereby provide improved flexibility and manipulation of a portion of the catheter within the vessel or cavity, said catheter comprising:

a one-piece elongate tube integrally formed of a material having sufficient stiffness to maintain said elongate tube along a substantially straight axis in the absence of an external force applied thereto, said one-piece elongate tube having a distal portion and a proximal portion, each of said portions having substantially the same outer circumference, and said distal portion being more flexible than said proximal portion.

2. A catheter according to claim 1, further comprising a medial portion of said one piece elongate tube between said distal and proximal portion, said medial portion being more flexible than said proximal portion and less flexible than said distal portion.

3. A catheter according to claim 2, wherein said proximal, medial, and distal portions of said one-piece elongate tube are welded together at ends thereof to thereby integrally form one-piece.

4. A catheter according to claim 1, wherein said distal portion of said one piece elongate tube converges to form a tip for ease of access into and through a body vessel, cavity, skin, or tissue.

5. A catheter according to claim 1, further comprising means within said one piece elongate tube for changing the angular attitude of said distal portion from said substantially straight axis to thereby remotely manipulate said distal portion of said catheter.

6. A catheter according to claim 1, further comprising means within said one piece elongate tube for changing the angular attitude of said proximal portion from said substantially straight axis separately from any changes in the angular attitude of said distal portion to thereby manipulate said medial portion of said catheter.

7. A catheter according to claim 1, further comprising a wire extending longitudinally through said one piece elongate tube for controlling a change in the angular attitude of said distal portion from said substantially straight axis to thereby remotely manipulate said distal portion of said catheter.

8. A catheter according to claim 1, further comprising a housing of such a size as to be readily held in the hand of a user and connected to said proximal portion of said one piece elongate tube to thereby provide control and manipulation of said elongate tube.

9. A catheter according to claim 1, wherein said material forming said one piece elongate tube is a polymeric material.

10. A catheter according to claim 1, wherein said proximal and distal portions of said one-piece elongate tube are integrally formed together as one piece by a radio frequency weld at common ends thereof.

11. A catheter for easily inserting into a vessel or cavity of the human body to thereby provide improved flexibility and manipulation of a portion of the catheter within the vessel or cavity, said catheter comprising:

a one-piece elongate tube integrally formed of a polymeric material, said one-piece elongate tube having a tubular proximal portion formed of a flexible polymeric material;

a tubular medial portion integrally formed coaxial and adjacent said proximal portion, and formed of a flexible polymeric material, said medial portion having substantially the same outer circumference as said proximal portion, and said medial portion being more flexible than said proximal portion; and a tubular distal portion integrally formed coaxial and adjacent said medial portion and on the opposite end of said medial portion from said integrally formed proximal portion, and formed of a flexible polymeric material, said distal portion having substantially the same outer circumference as said medial portion and said proximal portion, and said distal portion being more flexible than said medial portion.

12. A catheter according to claim 11, wherein said proximal, medial, and distal portions of said one-piece elongate tube are integrally formed from a single type of polymeric material.

13. A catheter according to claim 12, wherein said flexible polymeric material is a thermoplastic polymer.

14. A catheter according to claim 12, wherein said flexible polymeric material is polyurethane.

15. A catheter according to claim 11, wherein said proximal, medial, and distal portions of said one-piece elongate tube comprise separate pieces of polymeric material integrally joined to form a single elongate tube.

16. A catheter according to claim 11, further comprising a pair of lumens extending parallel to the axis of said coaxial proximal, medial, and distal portions, for providing a working channel from said proximal portion of said catheter to said distal portion.

17. A catheter according to claim 16, further comprising a pair of control wires extending longitudinally through said proximal, medial, and distal portions and parallel to the axis of said coaxial portions for bending and thereby manipulating said flexible portions when said control wires are moved longitudinally with respect to one another.

18. A catheter according to claim 17, wherein each of said control wires extends longitudinally from said proximal portion, through said medial portion, and into said distal portion, looped within said distal portion and extending longitudinally from said distal portion, through said medial portion, and into said proximal portion to thereby reduce slippage of said control wires as said wires are moved longitudinally with respect to one another.

19. A catheter according to claim 11, further comprising four control wires extending longitudinally through said proximal, medial, and distal portions and parallel to the axis of said coaxial portions for bending and thereby manipulating said flexible portions when said control wires are moved with respect to one another.

20. A catheter according to claim 19, wherein said control wires comprise two pairs of wires, each of said control wires extending longitudinally from said proximal portion, through said medial portion, and into said distal portion, looped within said distal portion and extending longitudinally from said distal portion, through said medial portion, and into said proximal portion to thereby reduce slippage of said control wires as said wires are moved longitudinally with respect to one another.

21. A catheter according to claim 11, wherein said proximal, medial, and distal portions of said one-piece elongate tube are integrally formed together as one piece by a radio frequency weld at respective common ends thereof.

22. A catheter for easily inserting into a vessel or cavity of the human body to thereby provide improved flexibility and manipulation of a portion of the catheter within the vessel or cavity, said catheter comprising:

a housing of such a size as to be readily held in the hand of a user;

a one-piece elongate tube integrally formed of a polymeric material, said one-piece elongate tube having a tubular proximal portion connected to and extending from said housing, said proximal portion formed of a flexible polymeric material; and a tubular distal portion coaxial and adjacent said proximal portion, and formed of a flexible polymeric material, said distal portion having substantially the same outer circumference as said proximal portion, and said distal portion being more flexible than said proximal portion;

control wires extending longitudinally through said proximal and distal portions and parallel to the axis of said coaxial portions for bending said flexible portions in response to movement of said control wires; and means carried by said housing for controlling the movement of said wires to thereby bend said flexible portions and remotely manipulate said catheter within a human body.

23. A catheter according to claim 22, further comprising a tubular medial portion coaxial and adjacent said proximal portion and said distal portion of said one-piece elongate tube, and formed of a flexible polymeric material, said medial portion having substantially the same outer circumference as said proximal portion and said distal portion of said one-piece elongate tube, and said medial portion being more flexible than said proximal portion and less flexible than said distal portion.

24. A catheter according to claim 23, further comprising a pair of lumens extending parallel to the axis of said coaxial proximal, medial, and distal portions, for providing a working channel from said proximal portion of said catheter to said distal portion.

25. A catheter according to claim 24, wherein said pair of lumens extend into said housing for accessing said lumens therefrom.

26. A catheter according to claim 22, wherein said wire control means comprises a rotating control wheel engaging a portion of each of said control wires so that rotation of said control wheel moves said wires and thereby changes the angular attitude of said distal portion of said elongate tube.

27. A catheter according to claim 22, further comprising a pair of control wires extending longitudinally through said proximal, medial, and distal portions and parallel to the axis of said coaxial portions for bending and thereby manipulating said flexible portions when said control wires are moved longitudinally with respect to one another.

28. A catheter according to claim 27, wherein each of said control wires extends longitudinally from said proximal portion, through said medial portion, and into said distal portion, looped within said distal portion and extending longitudinally from said distal portion, through said medial portion, and into said proximal portion to thereby reduce slippage of said control wires as said wires are moved longitudinally with respect to one another.

29. A catheter according to claim 22, further comprising four control wires extending longitudinally through said proximal, medial, and distal portions and parallel to the axis of said coaxial portions for bending and thereby manipulating said flexible portions when said control wires are moved with respect to one another.

30. A catheter according to claim 29, wherein said control wires comprise two pairs of wires, each of said control wires extending longitudinally from said proximal portion, through said medial portion, and into said distal portion, looped within said distal portion and extending longitudinally from said distal portion, through said medial portion, and into said proximal portion to thereby reduce slippage of said control wires as said wires are moved longitudinally with respect to one another.

* * * * *